United States Patent

Lin et al.

[11] Patent Number: 5,780,660
[45] Date of Patent: Jul. 14, 1998

[54] ZIRCONOCENE ISMERIZATION PROCESS

[75] Inventors: Ronny W. Lin; Troy E. DeSoto; John F. Balhoff, all of Baton Rouge, La.

[73] Assignee: Albemarle Corporation, Richmond, Va.

[21] Appl. No.: 744,334

[22] Filed: Nov. 7, 1996

[51] Int. Cl.$^6$ ............................. C07F 17/00; C07F 7/00
[52] U.S. Cl. .................. 556/11; 556/12; 556/53; 502/103; 502/117; 526/943
[58] Field of Search ................. 556/11, 12, 53; 526/943; 502/103, 117

[56] References Cited

U.S. PATENT DOCUMENTS

| | | | |
|---|---|---|---|
| 4,794,096 | 12/1988 | Ewen | 502/117 |
| 5,017,714 | 5/1991 | Welborn, Jr. | 556/12 |
| 5,036,034 | 7/1991 | Ewen | 502/117 |
| 5,145,819 | 9/1992 | Winter et al. | 502/117 |
| 5,296,434 | 3/1994 | Karl et al. | 502/117 |
| 5,302,733 | 4/1994 | Diefenbach et al. | 556/11 |
| 5,324,800 | 6/1994 | Welborn, Jr. et al. | 526/160 |
| 5,329,033 | 7/1994 | Spaleck et al. | 556/53 |
| 5,455,365 | 10/1995 | Winter et al. | 556/7 |
| 5,455,366 | 10/1995 | Rohrmann et al. | 556/8 |

*Primary Examiner*—Porfirio Nazario-Gonzalez
*Attorney, Agent, or Firm*—Philip M. Pippenger

[57] ABSTRACT

An essentially anhydrous agitated mixture of (i) finely-divided essentially anhydrous alkali metal fluoride (e.g., KF), (ii) haloaromatic compound having at least one halogen atom of atomic number greater than 9 on an aromatic ring (e.g., $C_6Cl_6$), and (iii) an aminophosphonium catalyst (e.g., $(Et_2N)_4PBr$), is heated at a temperature at which fluorine replaces one or more of the ring halogen atom of the haloaromatic compound.

33 Claims, No Drawings

ZIRCONOCENE ISMERIZATION PROCESS

TECHNICAL FIELD

This invention relates to processing of mixtures of meso and racemic forms of zirconocenes so as to convert at least a portion of the meso form to the racemic form.

BACKGROUND

Chiral zirconocenes are useful for the synthesis of polyolefins. The racemic form of these metallocenes provides stereoregular poly(alpha-olefins). In addition, the racemic form of zirconocenes are considerably more active as catalysts than the meso form, which produces only atactic polymers. Metallocenes and their use as catalysts in forming various olefin polymers are described, for example, in U.S. Pat. Nos. 4,794,096; 5,017,714; 5,036,034; 5,145,819; 5,296,434; 5,324,800; 5,329,033; 5,455,365; and 5,455,366, the full disclosures of which are incorporated herein by reference.

Processes for the synthesis of such zirconocenes tend to form mixtures of the meso and racemic forms. It would be most advantageous if a way could be found for effectively treating mixtures of meso and racemic zirconocenes so as to produce a product enriched in the desirable racemic mixture.

THE INVENTION

In accordance with this invention it has now been found possible to selectively isomerize meso zirconocenes to racemic zirconocenes. Moreover the isomerization can be conducted using meso and racemic zirconocene mixtures whereby the resultant product is enriched in the racemic form. The process of this invention thus makes it possible to maximize, or at least materially enhance, the efficiency of racemic zirconocene production processes.

Pursuant to this invention an isomerization process is provided which comprises producing a slurry of (i) a mixture of meso and racemic forms of a bridged zirconocene in (ii) a liquid ether-containing isomerization medium, and maintaining the resultant slurry at one or more temperatures at which at least a portion of the meso form of the zirconocene is isomerized to the racemic form to thereby form a racemate enriched zirconocene.

There are various ways of conducting this process. In one embodiment of this invention, the slurry is produced by combining the mixture of meso and racemic zirconocenes and the liquid ether-containing isomerization medium in proportions such that only a portion of the mixture of zirconocenes dissolves in the isomerization medium, and the resultant slurry is maintained at or brought to one or more suitable isomerization temperatures. In another embodiment, the slurry is produced by combining the mixture of meso and racemic zirconocenes and the liquid ether-containing isomerization medium in proportions such that the zirconocene mixture substantially completely dissolves in the isomerization medium. Then the resultant solution is concentrated (e.g., by vacuum evaporation of the ether medium) such that a solids phase appears in the ether medium.

In the systems studied to date, the racemic form of zirconocene is has been found to be less soluble in the liquid ether medium than the meso form of the zirconocene. Thus not only does this solubility difference keep more of the meso isomer in solution where it can be isomerized, but in addition the less soluble racemic form tends to precipitate out as a solids phase during the course of the isomerization. This in turn makes it possible during the isomerization period for additional meso isomer to progressively dissolve in the ether medium as the racemic form is progressively coming out of solution. And because the desired racemic form is in the solids phase, it is readily recovered from the liquid phase by conventional procedures such as decantation, centrifugation or filtration.

Typically the isomerization is performed at one or more temperatures in the range of about 20° C. to about 120° C., and preferably in the range of about 30° C. to about 70° C. The rate of isomerization tends to vary with temperature and thus is usually more rapid at higher temperatures and less rapid at lower temperatures. Accordingly, the isomerization reaction is performed for a period of time sufficient under the conditions employed to achieve a suitable or desired amount of isomerization. Typically isomerization periods fall in the range of about 0.5 to about 48 hours. With isomerization temperatures in the range of about 30° to about 70° C., periods in the range of about 1 to about 12 hours are preferred. It is particularly preferred to raise and lower the temperature of the isomerization mixture on at least two separate occasions (most preferably using at least three up and down cycles) during the course of the isomerization operation, with each of the changes in temperature, whether up or down, amounting to at least 15° C., while keeping the temperature within the overall isomerization temperature range. For example, if raising and lowering the temperature on two separate occasions, the temperature may first be raised to, say, 60° C. and then lowered to, say, 30° C., and then raised to say, 65° C., and then lowered to, say, 50° C.

It is desirable to agitate the isomerization mixture during at least a substantial portion of the isomerization reaction period.

Zirconocenes, such as are treated in accordance with this invention are mixtures of racemic isomers which have no plane of symmetry, and meso isomers which have a plane of symmetry running through the zirconium atom between the rings, and thus are achiral compounds. A few examples of such zirconocenes include:

[1,1'-dimethylsilanylenebis(methylcyclopentadienyl)] zirconium dichloride;
[1,1'-dimethylsilanylenebis(indenyl)]zirconium dichloride;
[1,1'-dimethylsilanylenebis(4,5,6,7-tetrahydroindenyl)] zirconium dichloride;
[1,1'-(1,1,2,2-tetramethyldisilanylene)bis (methylcyclopentadienyl)]zirconium dichloride;
[1,1'-(1,1,2,2-tetramethyldisilanylene)bis(4,5,6,7-tetrahydroindenyl)]zirconiumdichloride;
[1,1'-dimethylsilanylenebis (trimethylsilanylcyclopentadienyl)]zirconium dichloride;
[1,1'-(1,2,2-tetramethyldisilanylene)bis (trimethylsilanylcyclopentadienyl)]zirconium dichloride;
[1,1'-(1,1,3,3-tetramethyldisilanylene)bis(4,5,6,7-tetrahydroindenyl)]zirconiumdichloride;
[1,1'-(1,1,4,4-tetramethyl-1,4-disilanylbutylene)bis(4,5,6,7-tetrahydroindenyl)]zirconium dichloride;
[1,1'-(2,2-dimethyl-2-silapropylene)bis (methylcyclopentadienyl)]zirconium dichloride;
[1,2-ethylenebis(ethylcyclopentadienyl)]zirconium dichloride; and
[1,2-ethylenebis(indenyl)]zirconium dichloride.
Zirconocenes in which the halogen atoms are other than chlorine atoms can also be used, as well as zirconocenes in which either or both of the halogen atoms are replaced by other groups.

Preferred starting materials are mixtures of the racemic and meso forms of 1,1'-dihydrocarbylsilanylene-bridged zirconocenes, and more preferred are [1,1'-dimethylsilanylenebis(indenyl)]zirconium dihalides wherein, optionally, either or both of the indenyl groups is/are substituted by one or more alkyl groups. Mixtures of the racemic and meso forms of [1,1'-Dimethylsilanylenebis(methylindenyl)]zirconium dichlorides, especially [1,1'-Dimethylsilanylenebis(2-methylindenyl)]zirconium dichloride constitute particularly preferred starting materials for the isomerization process.

Ethers used in forming the isomerization medium preferably comprise cyclic and acyclic monoethers and polyethers that exist in the liquid state at, and preferably below, the lowest isomerization temperature to be used in the particular isomerization operation being conducted. However it is possible to employ ethers which exist in the solid state at the lowest isomerization temperature being used, provided such ethers are used in admixture with an additional inert liquid solvent such as a liquid hydrocarbon or a liquid tertiary amine in which the ether is soluble at the lowest isomerization temperature, so as to thereby provide a continuous liquid phase in which the isomerization is to be performed.

Typical ethers which may be used include acyclic ethers, such as dialkyl ethers, dicycloalkyl ethers, diaryl ethers, diaralkyl ethers, alkyl-arylethers, alkyl-cycloalkyl ethers, etc.; dialkylethers of diols such as dialkylethers of such diols as ethylene glycol, propylene glycol, 1,4-butanediol, etc.; trialkylethers of triols such as trialkylethers of glycerine, etc., dialkylethers of diethylene glycol; dialkylethers of triethylene glycol; dialkylethers of tetraethylene glycol; and similar liquid acyclic ethers. Preferred for use in forming the isomerization medium are cyclic ethers and polyethers having at least 5-membered rings, such as tetrahydrofuran, 2,3-benzofuran, alkyldihydrofurans, alkyltetrahydrofurans, alkyltetrahydrofurfuryl ethers, alkyldihydropyrans, tetrahydropyran, 1,4-dioxane, 1,3-dioxolane, and similar liquid cyclic ethers. When another type of inert solvent (e.g., an inert liquid hydrocarbon solvent, a liquid tertiary amine, a liquid mixture of hydrocarbon and tertiary amine, or the like) is used in combination with one or more ethers to form the isomerization medium, the resultant liquid medium preferably contains at least about 70% by volume, more preferably at least 80% and most preferably at least 90% by volume of the ether(s).

The proportions of as between the ether-containing liquid phase and the mixture of meso and racemic zirconocenes must be such as to form a slurry wherein a portion of the zirconocene is in solution and a portion of the zirconocene is in the form of solid particles in the continuous liquid phase. For efficient operation the proportions used will typically be such as to provide a slurry wherein the liquid phase contains an amount of solid particles falling in the range of about 3 to about 50 wt %, and preferably in the range of about 6 to about 25 wt %.

The manner by which the initial mixture of meso and racemic zirconocene isomers is produced or formed is not critical. What is important is that the initial mixture be amenable to treatment pursuant to this invention such that the racemic isomer content of the mixture can be increased by the practice of this invention.

The practice and advantages of this invention are demonstrated by the following examples which are presented for purposes of illustration and not limitation. Example 1 illustrates a procedure for producing a crude mixture of meso and racemic zirconocene. Example 2 illustrates a preferred procedure for treating a crude mixture in accordance with this invention.

EXAMPLE 1

In a dry box, 3.5 g of $ZrCl_4$ (0.015 gmol), 20 g of toluene and 2.0 g of TMEDA (N,N,N',N'-tetramethyl ethylenediamine; 0.017 gmol) were charged into a 100 cc flask. The slurry was heated up to 80° C. for 1 hour to form a $ZrCl_4$·TMEDA adduct, and the reaction mixture was then cooled down. To this mixture while still in the dry box were added 4.5 g of the dilithium complex of 1,1'-dimethylsilanylenebis(2-methylindene) diethyletherate powder (0.0112 gmol max.), 10 g of toluene and 3 g of tetrahydrofuran (THF; 0.04 gmol). The resultant slurry was stirred for 1 hour. The temperature of the slurry initially was about 27° C. (due to the heat of reaction) and during this one-hour period the slurry cooled to about 23° C. The slurry was then slowly heated up to 30° C., then 40° C. and finally to 80° C. over a period of 3 hours. After the orange slurry cooled down, the slurry was filtered and 2 g of toluene was used to wash the wet cake. After drying, 6.03 g of dry crude [1,1'-dimethylsilanylenebis(2-methylindenyl]zirconium dichloride was obtained with in which the meso/racemate ratio was 57.8/42.2 as shown by NMR.

EXAMPLE 2

In a dry nitrogen atmosphere, 2.1 g of the crude [1,1'-dimethylsilanylenebis(2-methylindenyl]zirconium dichloride produced in Example 1, and 9 g of THF in a 50 cc flask were stirred and heated up to reflux (at about 66° C.) for about 6 hours. During this time the heat was turned off 3 times to allow the reaction slurry to slowly cool down to 28° C., to 49° C. and to 40° C. After each such cooling, the heat was re-applied to bring the temperature back to reflux temperature to improve the efficiency of the isomerization. Then the orange slurry was slowly cooled down to room temperature, and then filtered under vacuum (in a dry box). 2 g of THF were used to wash the wet cake. After drying, 1.23 g of [1,1'-dimethylsilanylenebis(2-methylindenyl] zirconium dichloride was recovered, and this product was found to have a meso/racemate ratio of 2.0/98.0 as shown by NMR. The filtrate, after vacuum evaporation, amounted to 5 grams. Analysis of the combined filtrates from the THF isomerization treatment and from the subsequent 2 g wash of the high racemate content solids with THF showed the combined filtrates to contain 96.5 normalized wt % THF, 1.3 wt % TMEDA, 0.84 wt % toluene, 0.74 wt % of the racemic zirconocene and 0.63 wt % of the meso zirconocene.

Besides greatly enhancing the content of the racemic zirconocene in the recovered dry product, the limited amount of THF solvent used in Example 2 also dissolved most of the LiCl byproduct and excess $ZrCl_4$·TMEDA adduct contained in the crude [1,1'-dimethylsilanylenebis(2-methylindenyl]zirconium dichloride used as the feed in the isomerization process.

It is also noteworthy that the process of Example 2 gave a recovered yield of purified racemic zirconocene of about 66% based on the dilithium complex of 1,1'-dimethylsilanylenebis(2-methylindene) diethyletherate used in Example 1.

The materials referred to by chemical name or formula anywhere in the specification or claims hereof are identified as ingredients to be brought together in connection with performing a desired operation or in forming a mixture to be used in conducting a desired operation. Accordingly, even though the claims hereinafter may refer to substances in the present tense ("comprises", "is", etc.), the reference is to the substance, as it existed at the time just before it was first contacted, blended or mixed with one or more other substances in accordance with the present disclosure. The fact that a substance may lose its original identity through a chemical reaction, complex formation, solvation, ionization, or other transformation during the course of contacting, blending or mixing operations, if done in accordance with the disclosure hereof and with the use of ordinary skill of a chemist and common sense, is within the purview and scope of this invention.

Each and every patent or other publication referred to in any portion of this specification is incorporated in full into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process for treating a mixture of meso and racemic forms of a bridged zirconocene so as to produce a product enriched in racemic bridged zirconocene, which process comprises:
   a) combining (i) said mixture of meso and racemic forms of a bridged zirconocene, and (ii) a liquid ether-containing isomerization medium so as to form a mixture of (i) and (ii); and
   b) maintaining mixture of (i) and (ii) from a) at, or subjecting mixture of (i) and (ii) from a) to, one or more temperatures and for a period of time such that isomerization of meso bridged zirconocene to racemic bridged zirconocene takes place in said isomerization medium whereby a zirconocene enriched in racemic bridged zirconocene is formed.

2. A process according to claim 1 wherein the racemic form of zirconocene is less soluble in the liquid medium than the meso form of the zirconocene.

3. A process according to claim 1 wherein in b) at least a portion of the racemate-enriched zirconocene is in the form of a solids phase in said medium, and wherein the solids phase is recovered from the liquid medium.

4. A process according to claim 1 wherein said bridged zirconocene is at least one 1,1'-dihydrocarbylsilanylene-bridged zirconocene.

5. A process according to claim 1 wherein in a) a slurry of the bridged zirconocene in said liquid ether-containing isomerization medium is produced by combining said mixture of meso and racemic forms and said liquid ether-containing isomerization medium in proportions such that only a portion of said mixture dissolves in the isomerization medium.

6. A process according to claim 5 wherein in b) at least a portion of the racemate-enriched zirconocene is in the form of a solids phase in said medium.

7. A process according to claim 6 wherein the solids phase is recovered from the liquid medium.

8. A process according to claim 1 wherein in a) a slurry is produced by combining said mixture of meso and racemic forms and said liquid ether-containing isomerization medium in proportions such that all or substantially all of said mixture dissolves in the isomerization medium, and then concentrating the resultant solution such that a solids phase appears in said medium.

9. A process according to claim 8 wherein the solids phase in said medium comprises at least a portion of the racemate enriched zirconocene.

10. A process according to claim 9 wherein the solids phase is recovered from the liquid medium.

11. A process according to claim 1 wherein said bridged zirconocene is at least one 1,1'-dihydrocarbylsilanylene-bridged zirconocene; wherein in a) a slurry is produced by combining said mixture of meso and racemic forms and said liquid ether-containing isomerization medium in proportions such that only a portion of said mixture dissolves in the isomerization medium; wherein in b) at least a portion of the racemate-enriched zirconocene is in the form of a solids phase in said medium; and wherein the solids phase is recovered from the liquid medium.

12. A process according to claim 11 wherein said bridged zirconocene is a [1,1'-dimethylsilanylenebis(indenyl)] zirconium dihalide wherein, optionally, either or both of the indenyl groups is/are substituted by one or more alkyl groups; and wherein said liquid ether-containing isomerization medium consists essentially of at least one cyclic ether.

13. A process according to claim 12 wherein said cyclic ether is tetrahydrofuran.

14. A process according to claim 11 wherein said bridged zirconocene is a [1,1'-dimethylsilanylenebis(methylindenyl)]zirconium dichloride.

15. A process according to claim 14 wherein said liquid ether-containing isomerization medium consists essentially of at least one cyclic ether.

16. A process according to claim 15 wherein said cyclic ether is tetrahydrofuran.

17. A process according to claim 11 wherein said bridged zirconocene is [1,1'-dimethylsilanylenebis(2-methylindenyl)]zirconium dichloride.

18. A process according to claim 17 wherein said liquid ether-containing isomerization medium consists essentially of at least one cyclic ether.

19. A process according to claim 18 wherein said cyclic ether is tetrahydrofuran.

20. A process according to claim 1 wherein said bridged zirconocene is at least one 1,1'-dihydrocarbylsilanylene-bridged zirconocene; wherein in a) a slurry is produced by combining said mixture of meso and racemic forms and said liquid ether-containing isomerization medium in proportions such that all or substantially all of said mixture dissolves in the isomerization medium, and then concentrating the resultant solution such that a solids phase appears in said medium; wherein the solids phase in said medium comprises the racemate-enriched zirconocene; and wherein the solids phase is recovered from the liquid medium.

21. A process according to claim 20 wherein said bridged zirconocene is a [1,1'-dimethylsilanylenebis(indenyl)] zirconium dihalide wherein, optionally, either or both of the indenyl groups is/are substituted by one or more alkyl groups; and wherein said liquid ether-containing isomerization medium consists essentially of at least one cyclic ether.

22. A process according to claim 21 wherein said cyclic ether is tetrahydrofuran.

23. A process according to claim 20 wherein said bridged zirconocene is a [1,1'-dimethylsilanylenebis(methylindenyl)]zirconium dichloride.

24. A process according to claim 23 wherein said liquid ether-containing isomerization medium consists essentially of at least one cyclic ether.

25. A process according to claim 24 wherein said cyclic ether is tetrahydrofuran.

26. A process according to claim 20 wherein said bridged zirconocene is [1,1'-dimethylsilanylenebis(2-methylindenyl)]zirconium dichloride.

27. A process according to claim 26 wherein said liquid ether-containing isomerization medium consists essentially of at least one cyclic ether.

28. A process according to claim 27 wherein said cyclic ether is tetrahydrofuran.

29. A process according to claim 1 wherein said liquid ether-containing isomerization medium consists essentially of at least one cyclic ether.

30. A process according to claim 29 wherein said cyclic ether is tetrahydrofuran.

31. A process according to claim 30 wherein the bridged zirconocene is at least one 1,1'-dihydrocarbylsilanylene-bridged zirconocene.

32. A process according to claim 1 wherein in b) said mixture is subjected on at least two separate occasions to raised and lowered temperatures in which the changes in temperature, whether up or down, is at least 15° C., while at the same time keeping the temperature within the range of about 30° to about 70° C.

33. A process according to claim 32 wherein the bridged zirconocene is at least one 1,1'-dihydrocarbylsilanylene-bridged zirconocene, wherein said liquid ether-containing isomerization medium consists essentially of at least one cyclic ether, and wherein said mixture is subjected on at least three separate occasions to said raised and lowered temperatures such that there are at least three up and down cycles in temperature.

* * * * *

UNITED STATES PATENT AND TRADEMARK OFFICE
CERTIFICATE OF CORRECTION

PATENT NO. : 5,780,660
DATED : July 14, 1998
INVENTOR(S) : Ronny W. Lin, Troy E. DeSoto, John F. Balhoff It is certified that error appears in the above-identified patent and that said Letters Patent is hereby corrected as shown below:

Cover page, Item [57], The Abstract reads:

> An essentially anhydrous agitated mixture of (i) finely-divided essentially anhydrous alkali metal fluoride (e.g., KF), (ii) haloaromatic compound having at least one halogen atom of atomic number greater than 9 on an aromatic ring (e.g., $C_6Cl_6$), and (iii) an aminophosphonium catalyst (e.g., $(Et_2N)_4PBr$), is heated at a temperature at which fluorine replaces one or more of the ring halogen atom of the haloaromatic compound and should read:

> An isomerization process is described in which a slurry of a mixture of meso and racemic forms of a bridge zirconocene in a liquid ether-containing isomerization medium is formed and maintained at one or more temperatures for a period of time such that meso isomer is selectively isomerized to produce a racemate enriched zirconocene.

UNITED STATES PATENT AND TRADEMARK OFFICE
CERTIFICATE OF CORRECTION

PATENT NO.   :   5,780,660
DATED        :   July 14, 1998
INVENTOR(S)  :   Ronny W. Lin, Troy E. DeSoto, John F. Balhoff It is certified that error appears in the above-identified patent and that said Letters Patent is hereby corrected as shown below:

Cover page, Item [54], The Title reads:

ZIRCONOCENE ISMERIZATION PROCESS and should read:

ZIRCONOCENE ISOMERIZATION PROCESS

Signed and Sealed this

Twenty-first Day of September, 1999

*Attest:*

Q. TODD DICKINSON

*Attesting Officer*    Acting Commissioner of Patents and Trademarks